(12) United States Patent  (10) Patent No.: US 8,513,956 B2
Bevilacqua, Jr. et al.  (45) Date of Patent: Aug. 20, 2013

(54) CALIBRATION OF CONDUCTIVITY MEASUREMENT SYSTEM

(75) Inventors: Anthony C. Bevilacqua, Jr., Medford, MA (US); Robert P. Mansur, Chelmsford, MA (US); David W. Marsh, N. Scituate, RI (US); Xiaoxing Feng, Newton, MA (US); Richard G. Kunicki, Billerica, MA (US)

(73) Assignee: Mettler-Toledo Thornton, Inc., Bedford, MA (US)

( * ) Notice: Subject to any disclaimer, the term of this patent is extended or adjusted under 35 U.S.C. 154(b) by 321 days.

(21) Appl. No.: 12/843,387

(22) Filed: Jul. 26, 2010

(65) Prior Publication Data

US 2012/0019261 A1    Jan. 26, 2012

(51) Int. Cl.
*G01R 35/00*   (2006.01)
*G01N 27/02*   (2006.01)

(52) U.S. Cl.
USPC .......................................... 324/601; 324/439

(58) Field of Classification Search
USPC ........................................................ 324/601
See application file for complete search history.

(56) References Cited

U.S. PATENT DOCUMENTS

| 5,019,685 | A | * | 5/1991 | Nishimura | ................ 219/69.13 |
| 5,260,663 | A | | 11/1993 | Blades | |
| 5,334,940 | A | | 8/1994 | Blades | |
| 5,708,363 | A | | 1/1998 | Yates et al. | |
| 5,793,214 | A | * | 8/1998 | Wakamatsu | ................ 324/601 |
| 6,023,147 | A | * | 2/2000 | Cargin et al. | ................ 320/114 |
| 6,025,711 | A | * | 2/2000 | Demma et al. | .......... 324/207.26 |
| 6,621,413 | B1 | * | 9/2003 | Roman et al. | ............ 340/539.12 |
| 7,550,979 | B2 | | 6/2009 | Zhou et al. | |
| 2002/0153903 | A1 | * | 10/2002 | Murtishaw et al. | .......... 324/601 |
| 2003/0204962 | A1 | * | 11/2003 | Mangerson | ................ 33/366.15 |
| 2005/0200370 | A1 | | 9/2005 | Quackenbuch et al. | |
| 2007/0194792 | A1 | | 8/2007 | Quackenbush et al. | |
| 2009/0212788 | A1 | * | 8/2009 | Patterson | ...................... 324/601 |

FOREIGN PATENT DOCUMENTS

EP   1180694 A1   2/2002
JP   62-119465 A   5/1987

* cited by examiner

*Primary Examiner* — Jeff Natalini
(74) *Attorney, Agent, or Firm* — Standley Law Group LLP (57) ABSTRACT

A system and method for calibrating a digital conductivity and temperature measuring system. A connector is interposed between a sensor and transmitter of the digital conductivity and temperature measuring system. A calibrator, which may have selectable resistors with known values, is also attached to the connector. The sensor measures a raw resistance for a selected resistor. The digital conductivity and temperature measuring system then compares the raw resistance to the known value of the resistor to calculate a calibration factor.

30 Claims, 5 Drawing Sheets

CALIBRATION OF CONDUCTIVITY MEASUREMENT SYSTEM

BACKGROUND OF THE INVENTIVE FIELD

Exemplary embodiments of the invention described herein relate generally to measurement of electrical conductivity of fluids. More particularly, exemplary embodiments of the invention described herein relate to calibration of digital conductivity measuring systems.

Electrical conductivity measurements are commonly made in the laboratory, during an industrial process, and in other environments as a means of measuring, controlling, or monitoring chemical processes and ionic impurities. Such measurements have been made for over 100 years. Measuring electrical conductivity is a sensitive means of monitoring processes that can be measured by instrumentation capable of detecting from the ng/L to kg/L concentrations of ions.

Ions are chemical species which carry a net positive or negative charge and are, by definition, conductive. Though conductivity measurements are proportional to ionic concentration, conductivity measurements cannot distinguish the specific chemical concentration since all ions have different ion mobilities (ability or efficiency with respect to carrying a charge). However, for well understood applications with known chemicals, determining conductivity is an excellent analytical industrial tool for measuring ionic concentrations. In other applications such as high purity water treatment systems found in micro-electronics, life sciences, and power generation applications, conductivity is an excellent analytical tool for measuring ionic impurities.

A typical analog conductivity measurement system consists of a sensor in direct contact with a fluid to be measured. A separate micro-controlled transmitter that typically contains AC measurement electronics, a readout or other visual display, software menus for instrument control functions, and other means to communicate to external devices such as a programmable logic controller ("PLC") or data acquisition system used for industrial control systems is also typically present in such a conductivity measurement system. A cable, usually with a quick disconnect, is normally used to connect the transmitter to the sensor.

Therefore, a typical analog conductivity measurement system consists of a sensor, a transmitter, and a means of connection. Analog electrical conductivity (or resistivity=1/conductivity) measurement technology involves the use of an AC resistance measurement circuit connected to 2 (or more) electrically conducting electrodes. The electrodes are assembled in a mechanically rigid and unchanging geometrical configuration, separated by an electrically insulating material. The separation of the electrodes and the area of the electrodes in a fixed geometry are known traditionally as the sensor's "cell constant" ("cc"). To measure the conductivity of a fluid, the sensor is immersed in the fluid and the resistance of the fluid residing between the electrodes is measured by the AC resistance measurement circuit.

The resistance of the fluid between the electrodes is directly proportional to the distance between the electrodes. Therefore, resistance measurements need to be adjusted or normalized for the distance between the electrodes. Likewise the resistance of the fluid between the electrodes is inversely proportional to the surface area of the electrodes. Thus, the resistance measurement needs to be adjusted or normalized for the surface area of the electrodes. As a result, the measured resistance is adjusted, or normalized, for the cell constant, such that the cell constant=separation of the electrodes/surface area of the electrodes according to:

Resistivity=Resistance/cell constant and

Conductivity=1/Resistivity

It is conductivity that is proportional to the ionic concentration. The cell constant may be determined according to the other conventional procedures.

For analog sensors, a complete calibration of the measuring system is required to meet certain regulatory standards and/or good calibration practices. For analog sensors, the standard calibration practice is to disconnect the sensor from the measurement electronics, attach a resistor having a known value to the measurement electronics, and adjust the measurement electronics as necessary. Verification of analog sensors may also be conducted in a similar manner. For analog sensors, the sensor is disconnected from the measurement electronics and a resistor having a know value is attached to the measurement electronics. The output of the measurement electronics is compared to the resistance value of the resistor having a known value. If the comparison is within an acceptable limit, no calibration is needed.

This calibration technique of the measurement electronics is possible because the AC measurement electronics are typically located in the transmitter of analog conductivity measuring systems. This procedure may need to be repeated if a multiple-point calibration function is employed to calibrate a single circuit. This process may again need to be repeated if there are, as is usually the case, multiple AC resistance measurement sub-circuits embedded in the design. These sub-circuits may be utilized to provide multiple measurement ranges. Once the measurement circuit has been verified and/or adjusted, the traceable resistor is disconnected, and the sensor is reattached to the measurement electrodes. As used herein the term "traceable resistor" refers to a resistor having a known value.

The next step in the calibration process is to verify and/or adjust the cell constant of the sensor. To do this, the sensor is immersed in a solution of known and traceable conductivity, and then the cell constant of the sensor is calculated according to various computations:

New cc=old cc×(reference conductivity)/(measured conductivity)

or

New cc=(measured resistance)/(reference resistivity)

or

New cc=(measured resistance)*(reference conductivity)

In general, the calibration of the complete analog conductivity measurement system (both the measurement circuit and the cell constant), is then complete.

Digital conductivity sensors may also be used to measure conductivity. Digital conductivity sensors are functionally equivalent to analog conductivity sensors, but with multiple advantages. In analog conductivity sensors, the analog AC resistance signals are easily degraded by the length of the cable, external noise, and other means unless extraordinary precautions are taken. In contrast, the transmitter of a digital conductivity sensor has all the features of an analog conductivity transmitter, except the AC measurement circuit is directly attached to the sensor electrodes. A cable is still used to attach the transmitter to the sensor. However, the small separation (e.g., <1 inch) between the electrodes and the AC measurement system of the digital conductivity measuring system provides significant inherent measurement advantages, as well as better performance in terms of measurement range and accuracy in comparison to analog conductivity measuring systems. The AC measurement circuit of the digital conductivity measuring system converts all the analog signals to a digital signal, which can be transmitted by the cable to the transmitter over long distances without any signal degradation.

One of the challenges of the digital conductivity measuring system is that direct integration of the AC measurement circuit to the sensor prohibits subsequent disconnection of the measurement circuit from the sensor. More specifically, this integration of the measuring circuit and the sensor prevents calibration of the measuring circuit in the manner associated with calibration of an analog conductivity measuring system.

SUMMARY OF THE GENERAL INVENTIVE CONCEPT

Exemplary embodiments of the inventive concept are based upon the recognition that there is no known calibration and/or verification methodology, nor hardware or software calibration tools, for the electronic circuits of a digital conductivity measuring system. Furthermore, exemplary embodiments of the inventive concept are based upon the recognition that to comply with good calibration practices, and in some cases, to meet pharmaceutical compendia, calibration of the AC measurement circuit separate from the sensor cell constant is required. Therefore, exemplary embodiments described herein provide a system and method for accurately calibrating the electronic circuits of a digital conductivity measuring system, including calibration of the AC measurement circuit separate from the sensor cell constant.

Generally, the exemplary embodiments described herein provide a connector with three ports, in particular a Y-connector, interposed between the sensor and the transmitter of a digital conductivity measuring system. The transmitter may be connected to the Y-connector with a cable. The sensor includes the electrodes for an AC measurement circuit. The transmitter may have a display and user inputs. A calibrator is also connected to the Y-connector. The calibrator has a switch and at least one selectable resistor with a known value for each AC measurement range to be calibrated.

To calibrate the digital conductivity measuring system, an open circuit is created between the electrodes in the sensor. The open circuit may be created by allowing the electrodes to dry or by a sensor switch that electronically disconnects the electrodes from the measurement circuit. The transmitter then provides the calibration instructions to a user through the display. A traceable resistor is selected using the switch on the calibrator or a calibrator having a single resistor with a known value is attached. The user enters the known value of the resistor into the transmitter. The AC measuring circuit then measures the raw resistance of the selected resistor. The known value and the measured raw value are stored in a non-volatile memory of the transmitter and/or the sensor, and a calibration factor is calculated and stored in the non-volatile memory of the transmitter and/or the sensor. This provides the calibration factor for a sub-circuit. If more calibration values are needed for calibration of the sub-circuit, then the user selects a different resistor using the switch and the calibration steps are repeated. Therefore, each resistor can have a different known resistance value.

In digital conductivity measuring systems having multiple sub-circuits the steps may be repeated for each calibration value on each sub-circuit. Once all the calibration factors are stored in the memory, the Y-connector is removed, the cable leading from the transmitter is reattached to the sensor, and the digital conductivity measuring system is ready for operation.

In another configuration of a digital conductivity measuring system, the sensor may also include a resistance temperature device ("RTD"), or another suitable resistance-based temperature measuring device. To calibrate the temperature measuring circuit, which is a sub-circuit of the AC measurement circuit, the RTD is electrically disconnected from the measurement circuit by using a sensor switch interposed between the measurement circuit and the sensor. Once the RTD is disconnected from the measurement circuit, a temperature calibration mode may be entered. The transmitter then provides the user with calibration instructions through the transmitter display. A temperature resistor, having a known value, is selected using a switch on the calibrator or a calibrator having a single resistor with a known value is attached. The user may then enter the value of the resistor into the transmitter via the user interface. The temperature measurement circuit of the AC measurement circuit then measures the raw resistance of the resistor and stores both the raw resistance and the known temperature resistance value into the memory, as a calibration factor. If more temperature calibration points are needed the user either attaches a different calibrator or selects a different resistor and the calibration steps are repeated.

For a digital conductivity measuring system having a sensor with a temperature measuring device it is therefore possible to calibrate the temperature measuring circuit and/or the AC measuring circuit. The calibration of the temperature measuring circuit preferably takes place prior to the calibration of the measuring circuit.

The calibration method and system may also be used with digital conductivity measurement systems having wireless communication between the transmitter and the sensor. In this configuration, a connector is interposed between the sensor and the calibrator. After the electrodes and/or RTD are disconnected from the circuit, calibration may proceed as above.

The method and system described above may also be used to verify that the existing calibration of a digital conductivity measuring system is correct. During verification, the transmitter again displays a series of menu instructions to the user. The user then compares a measured resistance to a known or reference resistance value. In this case, no adjustments are made. Rather, only a comparison is provided to determine if a further adjustment is needed.

BRIEF DESCRIPTION OF THE DRAWINGS

In addition to the features mentioned above, other aspects will be readily apparent from the following descriptions of the drawings and exemplary embodiments, wherein like reference numerals across the several views refer to identical or equivalent features, and wherein.

DETAILED DESCRIPTION OF THE INVENTIVE CONCEPT

The present inventive concept will now be described more fully hereinafter with reference to the accompanying drawings, through which some, but not all possible embodiments of the invention are shown. Indeed, the present invention may be embodied in various forms and should not be construed as limited to the particular embodiments set forth herein.

Figure 1:
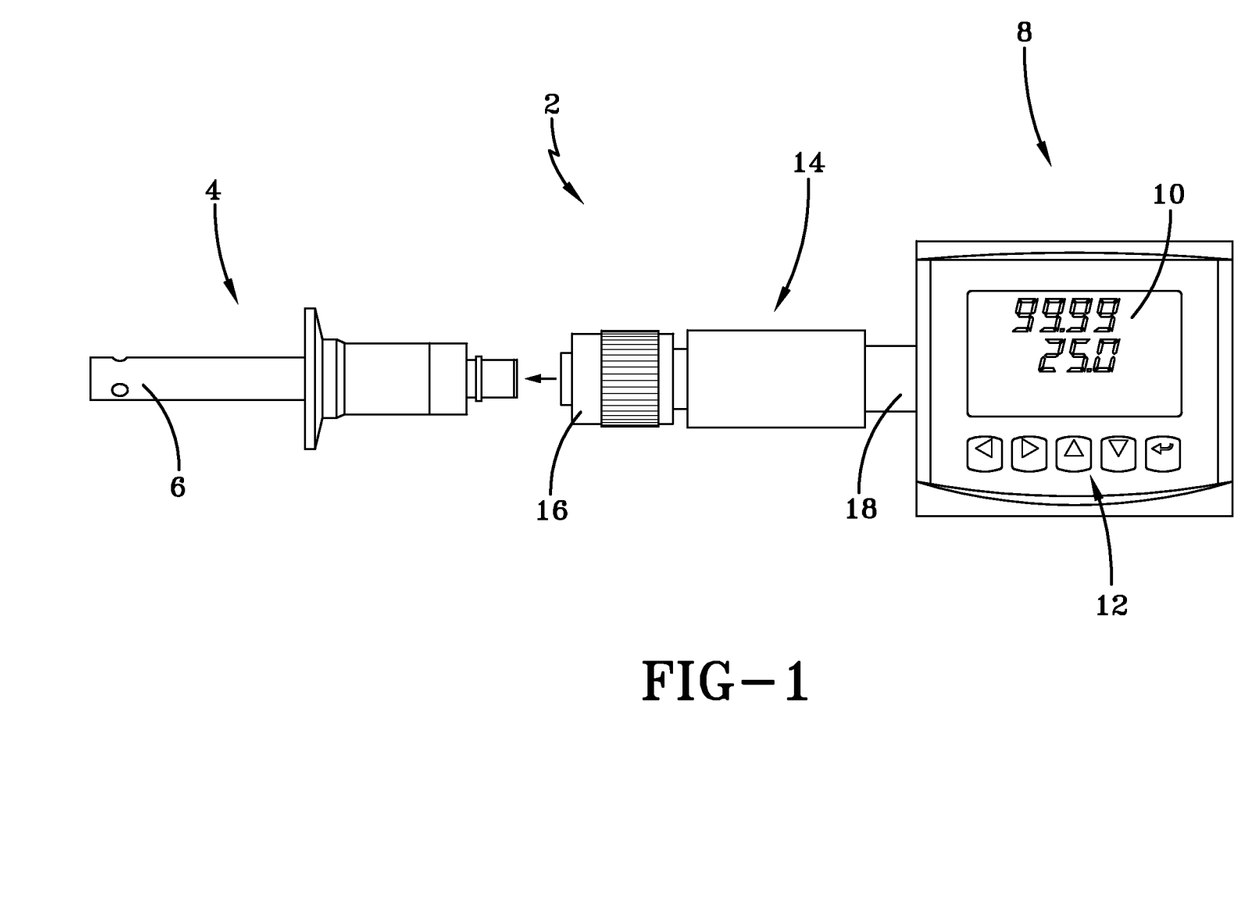
FIG. 1 is a diagram illustrating a typical digital conductivity measuring system that would benefit from exemplary embodiments of the system and method for calibration described herein.

FIG. 1 diagrammatically illustrates a digital conductivity measuring system 2, which may be usefully calibrated using exemplary embodiments of the system and method described herein. As shown, this digital conductivity measuring system 2 includes a sensor 4. The sensor 4 comprises two (or more) electrically conducting electrodes 6 and is designed to be placed in direct contact with the fluid to be measured. In such a digital conductivity measuring system 2, the AC measurement circuit 30 (shown in FIG. 3) may be directly attached to and housed in the sensor 4.

A microprocessor-controlled transmitter 8 is also provided and has a readout or a display 10, software menus for instrument control functions, and other means to communicate to external devices such as a PLC or data acquisition system used for industrial control systems. The transmitter 8 may also have a user interface 12, whereby a user may select options from the menu and input resistor values. The term transmitter 8 may be any device capable of performing the functions described herein. Specifically, the transmitter 8 may be any device capable of receiving a digital signal from the sensor 4, including, but not limited to, computer, PDA, smartphone, or other similar devices. A cable 14 is interposed between the sensor 4 and the transmitter 8 to facilitate their communication. The cable 14 has a first end 16 that connects to the sensor 4 and a second end 18 that connects to the transmitter 8. The cable 14 may have a quick disconnect feature that allows for easy removal and attachment of the cable 14 to both the sensor 4 and the transmitter 8.

The separation between the circuit 30 and the electrodes 6 is small, preferably less than one inch. This small separation provides significant inherent measurement advantages and also increases performance in terms of measurement range and accuracy. The circuit 30 converts all the analog signals to a digital signal, which can then be transmitted by the cable 14 over long distances to the transmitter 8 without any signal degradation.

Figure 2:
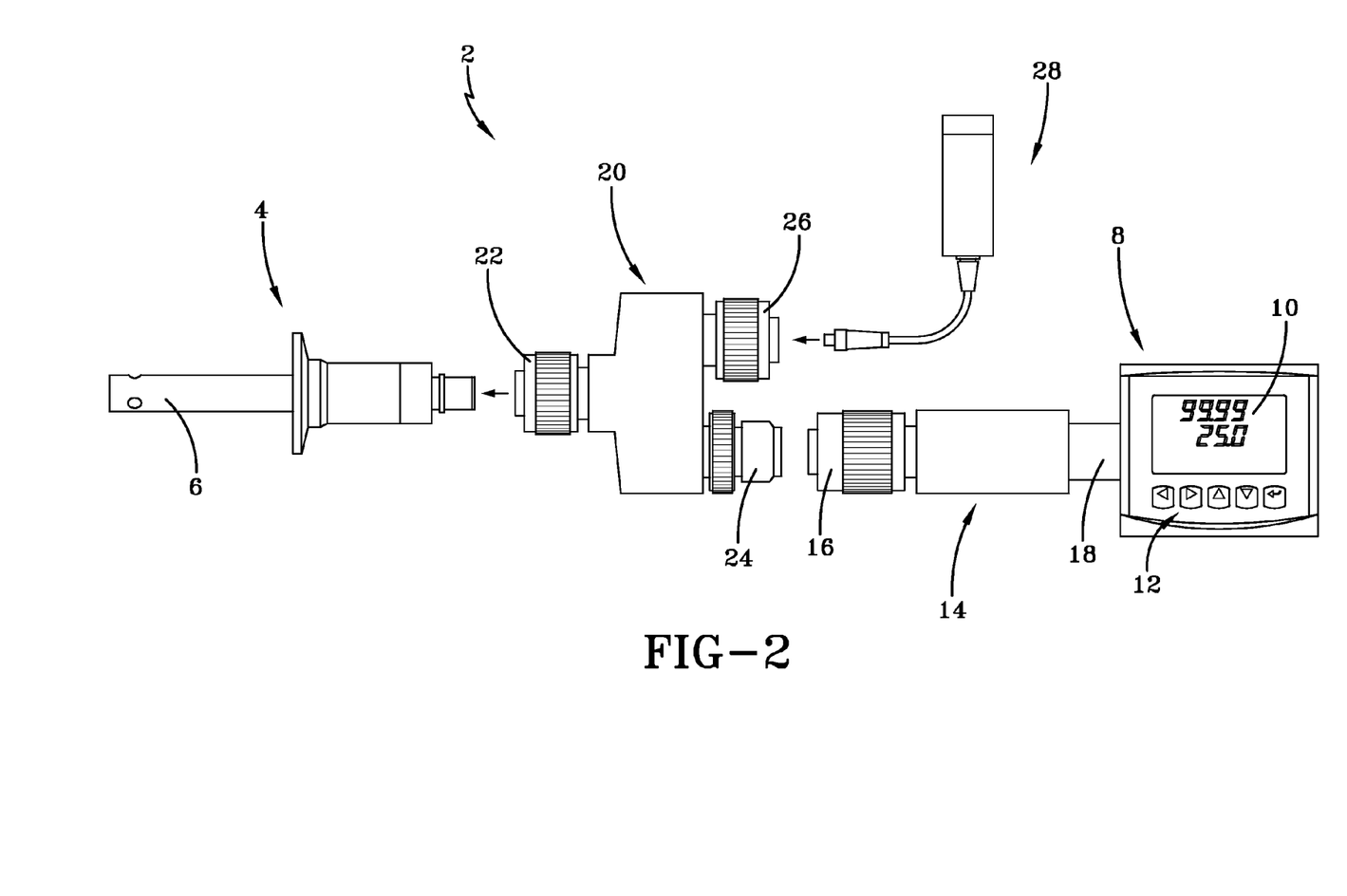
FIG. 2 is a diagram illustrating an exemplary embodiment of the system and method for calibration of a digital conductivity measuring system.
Figure 3:
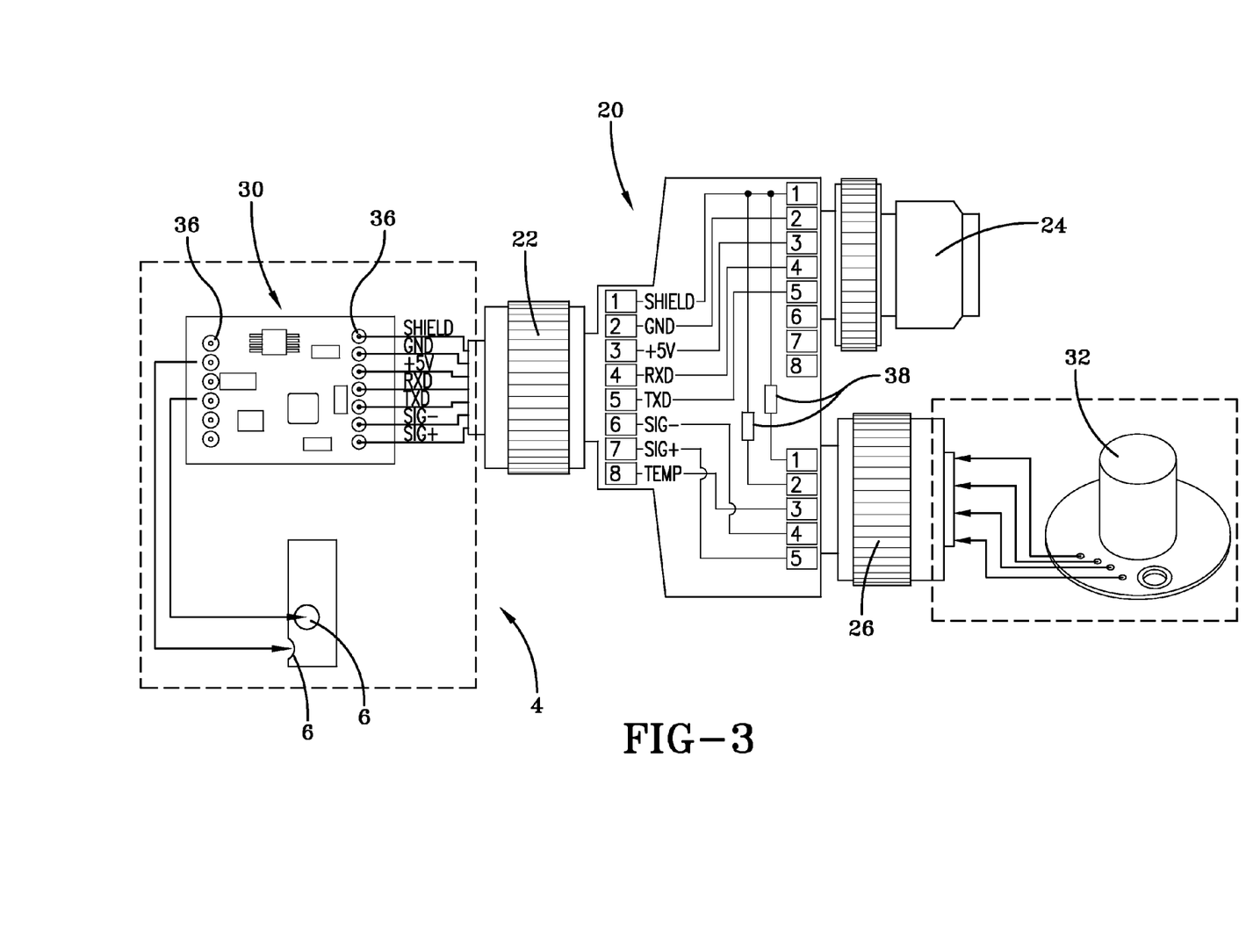
FIG. 3 is a simplified circuit diagram illustrating an exemplary embodiment of the system and method for calibration of a digital conductivity measuring system.

FIGS. 2 and 3 diagrammatically illustrate an exemplary embodiment of the inventive calibration system and method for a digital conductivity measuring system. FIG. 2 is a simple diagram illustrating the configuration of an exemplary embodiment of the inventive calibration system. FIG. 3 provides a simplified circuit diagram of an exemplary embodiment of the calibration system described herein.

To initiate calibration, it is first verified that the transmitter 8 is connected to the cable 14 at the second end 18. The sensor 4 is then removed from a fluid in which it is immersed such that an open circuit between the electrodes 6 is created. The sensor 4 is then disconnected from the first end 16 of the cable 14. In digital conductivity measuring systems 2 having an internal switch 42 (shown in FIG. 4) in the sensor 4, the sensor switch 42 may be used to disconnect the electrodes 6 from the AC measuring circuit 30, rather than removing the electrodes from a fluid.

A Y-connector 20 having a first port 22 at a first end, and a second port 24 and third port 26 at a second end, is provided and interposed between the sensor 4 and the transmitter 8. Although the term Y-connector is used herein, it should be understood to those of skill in the art that any connector having at least three ports may be used herewith, including, but not limited to, a T-connector. The Y-connector 20 is attached to the sensor 4 at the first port 22. The first end 16 of cable 14 is attached to the second end of the Y-connector 20 at the second port 24. A calibrator 28 is attached to the second end of the Y-connector 20 at the third port 26. The calibrator 28 is a device that contains a traceable resistor. In other exemplary embodiments the calibrator 28 may contain a collection of traceable resistors and a switch 32 provided therewith may be used to select an individual resistor to be connected to a circuit to be calibrated. As used herein the term "resistor" is used to denote a resistor or its functional equivalent, including, but not limited to, electrical simulated resistors and switch capacitors.

The Y-connector 20 connects the selected resistance from the calibrator 28 to the AC measurement circuit 30 (see FIG. 3). The AC measurement circuit 30 has 2 pairs of signal pins 36. One pair is connected to the electrodes 6, while the other pair is connected to the SIG+ and SIG− outputs that connect to the selected resistors on the calibrator 28. In some exemplary embodiments, the sensor 4 may have extra connectors to provide a means to connect the resistor(s) in the calibrator 28 to the AC measurement circuit 30. In some exemplary embodiments, the Y-connector 20 may have at least one shielding resistor 38. The shielding resistor 38 reduces electrical noise during the calibration process.

In the configuration shown in FIG. 2, the AC measurement circuit 30 is connected to the sensor electrodes 6 and the calibrator 28 resistor(s) in parallel. If the sensor electrodes 6 are dry, there is open circuit resistance between the electrodes 6. Thus, the measured resistance is equal to that of the resistor selected in the calibrator 28.

Once the calibration system is properly connected, the transmitter display 10 may prompt the user to select the calibration function. In other exemplary embodiments, the transmitter 8 may enter calibration mode automatically after connection to the Y-connector 20 and calibrator 28 has been made. To calibrate the digital conductivity measuring system 2, the menu driven software in the transmitter 8 instructs a user to select a resistor of a nominal, but known value, $R_{1ref}$. The user selects the resistor via the switch 32 on the calibrator 28, or by attaching a calibrator having a single resistor with the corresponding known value, $R_{1ref}$. The value of the resistors within the calibrator 28 is selected to be within the operating range of the sub-circuit to be calibrated.

There may be multiple sub-circuits in the complete measurement circuit 30. A first sub-circuit, C1, is selected and the firmware of the transmitter and the sensor forces the circuit 30 to measure using the sub-circuit, C1. The traceable value of the resistor, $R_{1ref}$, may then be entered into the transmitter 8, by using the user interface 12. The measurement circuit 30 measures and reports the raw resistance, $R_{1meas}$, using the selected sub-circuit, C1. The two resistance values, $R_{1ref}$ and $R_{1meas}$ are stored in a memory of the transmitter 8 and/or sensor 4.

To properly calibrate a digital conductivity measuring system, it may be necessary to use multiple calibration values for each sub-circuit. If multiple calibration values are necessary, the menu driven software in the transmitter 8 instructs a user to select a second resistor in the calibrator 28, $R_{2ref}$, via the switch 32. In exemplary embodiments where the calibrator 28 contains only a single traceable resistor, a calibrator 28 having a resistor having a known value corresponding to $R_{2ref}$ may be used. The firmware in the digital conductivity measuring system 2 forces the measurement circuit 30 to remain on sub-circuit C1. The user then enters the new traceable value of the resistor, $_{R2ref}$, and the measurement circuit 30 measures and reports the raw resistance, $_{R2meas}$, using the sub-circuit C1. The two new resistance values, $R_{2ref}$ and $R_{2meas}$, are then stored in the memory of the transmitter 8 and/or sensor 4. These steps may be repeated for as many calibration values as required for sub-circuit C1. The digital conductivity measuring system 2 then mathematically determines the calibration factors and stores the calibration factors in the non-volatile memory in the sensor 4 and/or in the transmitter 8. This may be repeated for each sub circuit C2, C3, C4 . . . Cn present, as required for compete calibration of the AC measurement circuit 30.

After calibration of the digital conductivity measuring system 2 is complete, the Y-connector 20 is disconnected from the sensor 4 and the cable 14, and the sensor 4 is reattached to the cable 14. After the digital conductivity measuring system 2 is reassembled, it is ready to resume operation. The above system and method may also be employed to verify the accuracy of the circuit. Using similar menu driven software, one would compare the measured resistance to a known or reference resistance value. In this case, there is no adjustment, only a comparison to determine if a further adjustment is needed.

Figure 4:
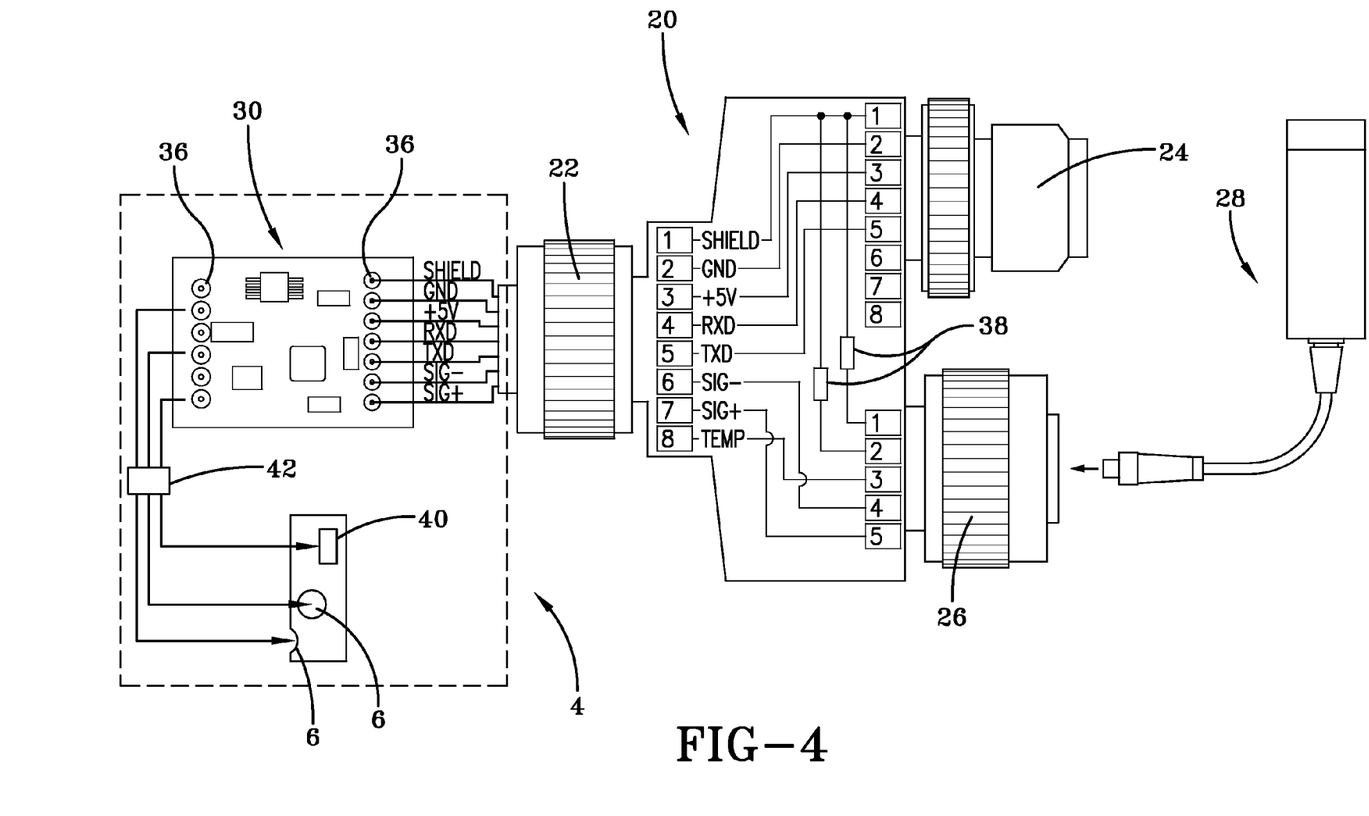
FIG. 4 is a simplified circuit diagram illustrating an exemplary embodiment of the system and method for calibration of a digital conductivity measuring system having a RTD.

FIG. 4 diagrammatically illustrates an exemplary embodiment of the inventive calibration system and method for a digital conductivity measuring system wherein the sensor 4 includes electrodes 6 and a RTD 40 as temperature measuring device. As shown in FIG. 4, the electrodes 6 and the RTD 40 are in electrical communication with the AC measurement circuit 30, which includes a temperature measuring circuit. The AC measurement circuit 30 is connected to a calibrator 28 by way of Y-connector 20. As with other configurations of the digital conductivity measuring systems 2, if the sensor electrodes 6 are dry, there is an open circuit resistance between the electrodes 6. Thus, the measured resistance is equal to that of the selected resistor, and the AC measurement circuit 30 may be calibrated as described above.

As described in more detail below, configurations of the digital conductivity measuring system 2 having an optional sensor switch 42 (as shown in FIG. 4) may also be calibrated using the system and method described herein without the need to remove the electrodes 6 from the fluid to be measured. It should be understood by those of skill in the art that the sensor switch 42 may be used in combination with any exemplary embodiment of the calibration system and method described herein.

As shown in FIG. 4, the measurement circuit 30 is connected to the sensor 4, including electrodes 6 and the RTD 40, and to the calibrator 28. The calibrator 28 includes a single resistor having a known value. In other exemplary embodiments, the calibrator 28 may include a plurality of resistors having known values individually selectable using the switch 32. In digital conductivity measuring systems having an RTD 40, the calibrator may have at least one resistor for calibrating the RTD 40.

In digital conductivity measuring systems 2 having the optional sensor switch 42, the sensor switch 42 may be interposed between the sensor 4 and the measuring circuit 30. The sensor switch 42 may be integrated into the measurement circuit 30 or it may be placed in-line between the measurement circuit 30 and the sensor 4. The sensor switch 42 is used to remove the electrodes 6 and the RTD 40 from the circuit for calibration. Once the electrodes 6 are removed from the circuit, calibration of the measuring circuit 30 may proceed as described above. Similarly, the calibration of the temperature measuring circuit for the RTD 40 may also be calibrated once it is disconnected from the circuit.

As with the conductivity calibration, the transmitter display 10 may prompt a user to select the temperature calibration function. In other exemplary embodiments, the transmitter 8 may enter temperature calibration mode after the calibrator 28 is placed in circuit. To calibrate the temperature feature of a digital conductivity measuring system 2, the menu driven software in the transmitter 8 instructs the user to select a resistor for calibrating the RTD 40, having a known resistance value, $R_{1Tref}$. The user selects the resistor via the switch 32 on the calibrator 28. In exemplary embodiments using a calibrator 28 having a single resistor, the user may attach a calibrator 28 having a resistor for calibrating the RTD 40, with resistance value $R_{1Tref}$. After the resistor is placed in the circuit, the temperature resistance, $R_{1Tref}$, may then be entered into the transmitter 8, by using the interface 12. The measurement circuit 30 measures and reports the raw temperature resistance, $R_{1Tmeas}$. The two temperature resistance values, $R_{1Tref}$ and $R_{1Tmeas}$, are stored in the memory of the transmitter 8 and/or the sensor 4 as a temperature calibration value.

To properly calibrate the temperature measuring circuits of the measurement circuit 30, it may be necessary to use multiple calibration values. If multiple calibration values are necessary, the menu driven software in the transmitter 8 instructs a user to select a second resistor having a known value. A resistor having a different known value is attached, either by attaching a different calibrator 28 or by selecting a new resistor using switch 32. The two temperature resistance values, $R_{2Tref}$ and $R_{2Tmeas}$, are stored in the memory of the transmitter 8 and/or sensor 4 as the second temperature calibration value. This may be repeated as necessary until the temperature measuring circuit of the measurement circuit 30 is calibrated.

Figure 5:
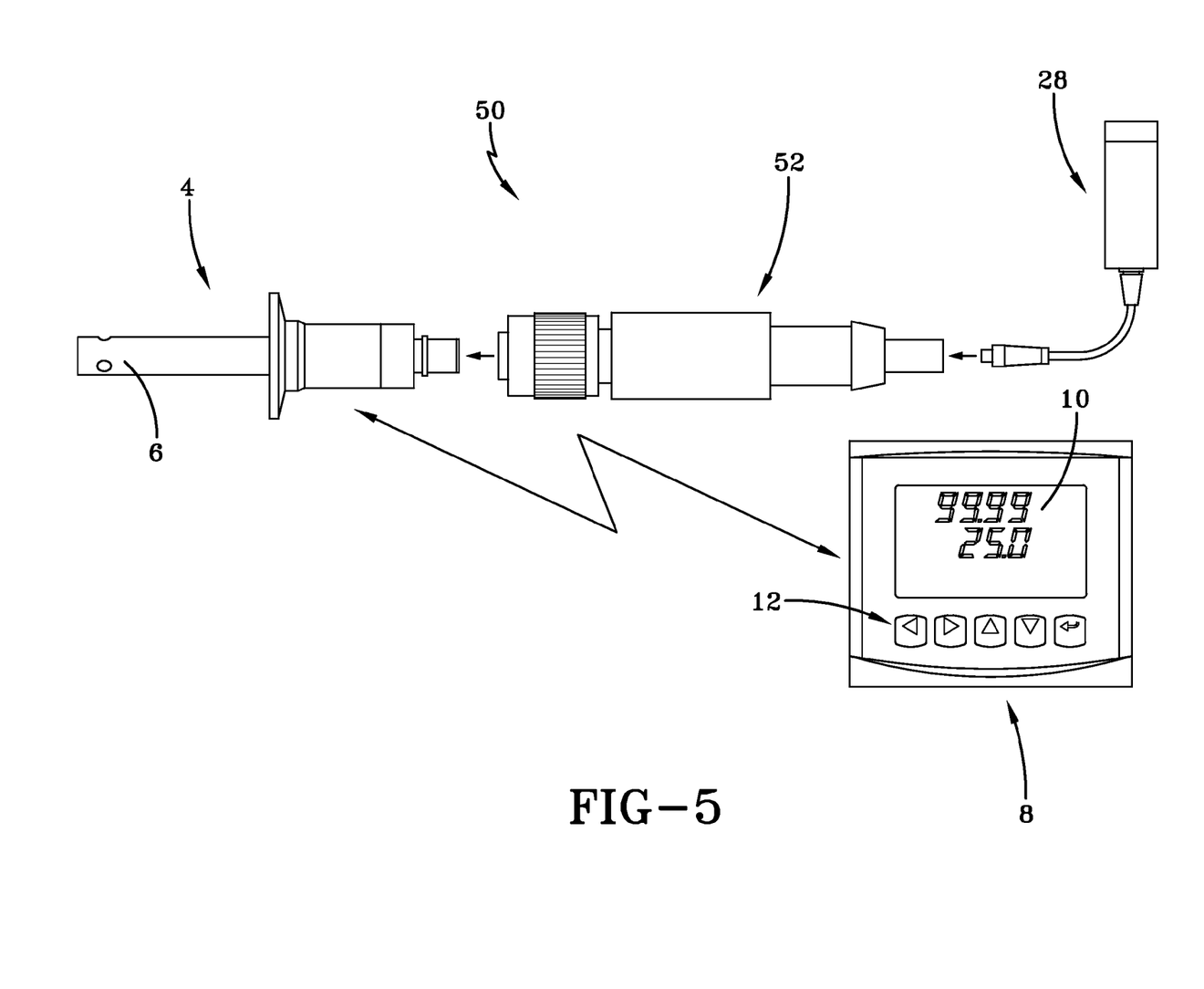
FIG. 5 is a diagram illustrating a digital conductivity measuring system, having a sensor and transmitter in wireless communication that would benefit from exemplary embodiments of the system and method for calibration described herein.

Other configurations of a digital conductivity measuring system 50 may have wireless communication between the sensor 4 and the transmitter 8, as shown in FIG. 5. To calibrate the wireless digital conductivity measuring system 50, a connector 52 is interposed between the sensor 4 and the calibrator 28. Once the electrodes 6 have been removed from the circuit, either by allowing the electrodes to dry or by use of the switch 42, calibration of the wireless conductivity measuring system 50 may proceed as described above. Wireless digital conductivity measuring system 50 may also include a RTD 40. Once the RTD 40 has been disconnected from the circuit using a sensor switch 42, calibration of the measuring circuit for the RTD 40 may also proceed as described above.

To guide a user through the calibration process described herein the transmitter 8 and/or sensor 4 may be pre-programmed. The programming may include the displayed user instructions and prompts for the entering of resistor values. Further, the programming may include hardware details to determine the number of calibration values necessary for each sub-circuit, and the number of sub-circuits. The number of sub-circuits may be automatically selected or entered manually by the user. The programming may also force the calibration of all calibration values on a specific sub-circuit before allowing calibration of addition sub-circuits to ensure proper calibration of the digital conductivity measuring system. This programming may either be stored in the non-volatile memory in the sensor 4 and/or the transmitter 8, and may be upgradable to adapt to different transmitters 8, calibrators 28 and sensors 8.

Although the invention has been described by presenting specific exemplary embodiments, it is evident that numerous further variants could be created based on a knowledge of the present invention, for example by combining the features of the individual exemplary embodiments with each other and/or by interchanging individual functional units between the embodiments. Therefore, while certain exemplary embodiments of the present invention are described in detail above, the scope of the invention is not to be considered limited by such disclosure, and modifications are possible without departing from the spirit of the invention as evidenced by the following claims:

What is claimed is:

1. A method for calibrating a digital conductivity measuring system having a transmitter in electrical communication with a sensor, said sensor having a measurement circuit and electrodes therein, said method comprising:
   interposing a connector between said transmitter and said sensor;
   attaching a calibrator to said connector, said calibrator having at least one resistor of a known value;
   measuring a raw resistance for said at least one resistor; and
   comparing the known value of said at least one resistor and the measured raw resistance to determine a first calibration factor.

2. The method of claim 1, wherein said transmitter includes a display, and a user interface.

3. The method of claim 2, further comprising displaying a menu on said display, said menu providing a user with calibration instructions.

4. The method of claim 1, further comprising interposing a cable between said transmitter and said connector.

5. The method of claim 1, wherein said measurement circuit includes at least one sub-circuit.

6. The method of claim 5, further comprising isolating each sub-circuit for calibration.

7. The method of claim 6, further comprising repeating calibration for each said sub-circuit to provide a series of calibration points for each said sub-circuit.

8. The method of claim 1, wherein each resistor has a different known resistance value.

9. The method of claim 1, wherein the known value of the at least one resistor is within a range measurable by the measurement circuit.

10. The method of claim 1, wherein the connector includes at least one shielding resistor.

11. The method of claim 1, further comprising providing a sensor switch interposed between said electrodes and said measurement circuit.

12. A method for calibrating a digital conductivity measuring system having a transmitter with a display and a user interface, a sensor that includes electrodes, a temperature measuring device, and a measurement circuit, said transmitter in communication with said sensor, said method comprising:
   providing a calibration system, said calibration system including:
      a connector, said connector having at least a first end with a first port, and a second end with a second port, and
      a calibrator, said calibrator including at least one resistor of known value;
   isolating said electrodes and said temperature measuring device from said measurement circuit;
   attaching said digital conductivity measuring system sensor to said first port of said connector;
   attaching said calibrator to said second port of said connector;
   displaying a menu on said display of said transmitter, said menu providing a user with calibration instructions;
   selecting said at least one resistor of said calibrator;
   entering a known value of the selected calibrator resistor into said transmitter;
   measuring a raw resistance for the selected at least one resistor;
   storing the known value of the selected resistor and said raw resistance in a memory;
   determining mathematical calibration factors; and
   storing said calibration factors in the memory.

13. The method of claim 12, wherein said transmitter is in wireless communication with said sensor.

14. The method of claim 12, wherein said calibrator includes a switch that permits selection between each resistor present.

15. The method of claim 12, further comprising providing a sensor switch to create an open circuit between said electrodes, said temperature measuring device, and said measurement circuit.

16. The method of claim 12, wherein said connector includes a third port on said second end.

17. The method of claim 16, further comprising connecting said transmitter to said connector using a cable having a first end and second end.

18. A system for calibrating a digital conductivity measuring system that includes a sensor with at least two electrodes, a measurement circuit, a transmitter having a display, a user interface, and a memory device of the sensor and/or the transmitter, said transmitter in communication with said sensor, said system comprising:
   a connector having a first end with a first port, and a second end with a second port, said connector adapted for attachment to said sensor of said digital conductivity measuring system at said first port thereof; and
   a calibrator, said calibrator having at least one resistor of known resistance, said calibrator adapted for attachment to said connector at said second port thereof such that said at least one resistor of known resistance will be connected to the measurement circuit;
   wherein, when said connector, said sensor and said calibrator are so connected and said at least two electrodes are placed in an open circuit, said measurement circuit will be made to measure the resistance of said at least one resistor of known resistance to provide a measured resistance value for comparison to the known resistance value of the at least one resistor of known resistance to determine a calibration factor.

19. The system of claim 18, wherein said transmitter is adapted for wireless communication with said sensor.

20. The system of claim 18, wherein said connector further comprises a third port on said second end.

21. The system of claim 20, wherein said transmitter is connected to said connector at the third port thereof by a cable interposed between said transmitter and said connector.

22. The system of claim 18, wherein said display is adapted to present calibration instructions to a user.

23. The system of claim 18, wherein said measurement circuit has at least one sub-circuit.

24. The system of claim 23, wherein said system is adapted to isolate each sub-circuit for calibration.

25. The system of claim 18, wherein said measurement circuit is adapted to measure a raw resistance for each resistor of known resistance.

26. The system of claim 18, wherein said calibrator includes a switch permitting selection between each resistor present in said calibrator.

27. The system of claim 18, further comprising a sensor switch interposed between said at least one electrode and said measurement circuit, said sensor switch electronically isolating said electrodes from said measurement circuit when activated.

28. The system of claim 18, wherein said digital conductivity measuring system includes a temperature measuring device in said sensor that is in communication with said measurement circuit.

29. The system of claim 28, further comprising a sensor switch interposed between said temperature measuring device and said measurement circuit, said sensor switch electronically isolating said temperature measuring device from said measurement circuit when activated.

30. The system of claim 18, wherein said connector includes at least one shielding resistor.

* * * * *